United States Patent [19]

Silvestrini

[11] Patent Number: 5,041,446

[45] Date of Patent: Aug. 20, 1991

[54] METHOD FOR INHIBITING THE DEVELOPMENT OF TOLERANCE IN THE ANALGESIC TREATMENT WITH MORPHINE

[75] Inventor: Bruno Silvestrini, Rome, Italy

[73] Assignee: Aziende Chimiche Riunite Angelini Francesco A.C.R.A.F. S.p.A., Rome, Italy

[21] Appl. No.: 362,755

[22] Filed: Jun. 6, 1989

[30] Foreign Application Priority Data

Oct. 6, 1988 [IT] Italy ............................... 48071 A/88

[51] Int. Cl.$^5$ ............................................ A61K 31/495
[52] U.S. Cl. ..................................................... 514/255
[58] Field of Search ........................................... 514/255

[56] References Cited

U.S. PATENT DOCUMENTS 4,252,721 2/1981 Silvestrini et al. ................... 514/913

Primary Examiner—Stanley J. Friedman
Attorney, Agent, or Firm—Ladas & Parry

[57] ABSTRACT

Method for inhibiting the development of tolerance in the analgesic treatment with morphine of a subject in need of said treatment, comprising administering systemically and contemporarily an effective analgesic dose of morphine and an amount of dapiprazole of from ¼ to 1 part by weight to 1 part by weight of said analgesic dose of morphine.

Pharmaceutical composition useful in the said method.

4 Claims, No Drawings

METHOD FOR INHIBITING THE DEVELOPMENT OF TOLERANCE IN THE ANALGESIC TREATMENT WITH MORPHINE

This invention relates to the a method for inhibiting the development of tolerance in the analgesic treatment with morphine and to a pharmaceutical composition useful in said method.

It is known that morphine is a potent analgesic drug used to relieve severe and persistent pain in subjects suffering from incurable diseases. Tolerance develops rapidly after administration of morphine both by mouth and injection. Increased doses are therefore necessary to produce the desired analgesic effect as the treatment continues.

3-(2-(4-(2-methylphenyl)-1-piperazinyl) -ethyl)-5,6,7,8-tetrahydro-1,2,4-triazole(4,3-a)pyridine hydrochloride, known as dapiprazole, has been disclosed by U.S. Pat. No. 4,252,721 as useful in the treatment of abstinence syndrome in subjects addicted to or dependent from alcohol, smoke and various drugs, at an average dose of from 25 to 50 mg three times a day.

Other known compounds useful in the treatment of the abstinence syndrome are clonidine and benzodiazepines. However, no compound useful in the treatment of the abstinence syndrome has so far been disclosed as useful in inhibiting tolerance.

It has now been surprisingly found that dapiprazole inhibits the development of tolerance when administered by systemic route contemporarily with morphine thus reducing the increase in daily administration of morphine to produce the desired analgesic effect as the treatment continues. The amount of dapiprazole which proved to be effective in inhibiting the development of tolerance to morphine is of from $\frac{1}{4}$ to 1 part by weight to 1 part by weight of morphine.

The analgesic effective dose of morphine varies according to the severity of the disease, the weight of the subject and other parameters well known to the people skilled in the art. Such a dose is, however, generally of from 8 to 20 mg. The amount of dapiprazole administered contemporarily with morphine according to the present invention is therefore usually of from 2 to 20 mg either in separate dosage forms or in the same dosage form.

An object of this invention is, therefore, a method for inhibiting the development of tolerance in the analgesic treatment with morphine of a subject in need of said treatment, comprising administering systemically and contemporarily an effective analgesic dose of morphine and an amount of dapiprazole of from $\frac{1}{4}$ to 1 part by weight to 1 part by weight of said analgesic dose of morphine.

Another object of this invention is a pharmaceutical composition comprising an amount of dapiprazole effective in inhibiting the development of tolerance, together with a pharmaceutically acceptable carrier. Preferably, the pharmaceutical composition of this invention will comprise from 2 to 20 mg of dapiprazole or the equivalent amount of a pharmaceutically acceptable acid addition salt thereof. Even more preferably the pharmaceutical composition of this invention will comprise an effective analgesic amount of morphine and an amount of dapiprazole of from $\frac{1}{4}$ to 1 part by weight to 1 part by weight of said analgesic amount of morphine, together with a pharmaceutically acceptable carrier.

Both morphine and dapiprazole are preferably used in the form of hydrochloride salts. In this description and in the claims the terms "morphine" and "dapiprazole" also embrace their pharmaceutically acceptable acid addition salts.

The pharmaceutical compositions of this invention can be solid, such as for example tablets, pills and capsules, or liquid such as for example solutions and are prepared according to known methods.

In addition to the carriers they can also contain usual pharmaceutical additives such as for example preservatives, stabilizers, buffers, dyes and flavours.

The pharmacological evaluation showed that dapiprazole does not influence the analgesic effect of morphine when the two compounds are administered simultaneously ( EXPERIMENT A). The acute toxicity study on female mouse showed that LD after subcutaneous administration of combinations containing various ratios of dapiprazole hydrochloride (DH) to morphine hydrochloride (MH) is 565 mg/Kg of DH+126 mg/Kg of MH, 386 mg/Kg of DH+230 mg/Kg of MH, 245 mg/Kg of DH+328 mg/Kg of MH and 146 mg/Kg of DH+522 mg/Kg of MH, respectively; in the same study LD of DH alone and MH alone were 645 and 576 mg/Kg, respectively (EXPERIMENT B). It will be recognized that the above LD relates to combinations containing about 4.4, 1.7, 0.7 and 0.28 parts by weight of DH to 1 part by weight of MH.

A preliminary study in man showed that the increase in daily administration to patients receiving simultaneously from 2,5 to 10 mg of dapiprazole hydrochloride and 10 mg of morphine hydrochloride as many times a day as required by their pain syndrome for 2 months were significantly lower than in patients receiving 10 mg of morphine hydrochloride alone (EXPERIMENT C).

EXPERIMENT A

The influence of dapiprazole on the analgesic activity of morphine was studied using the phenylquinone-induced writhing test according to the method of Hendershot and Forsaith (J. Pharmacol. Exp. Ther. 125:237, 1979 ) modified.

Alogenic agent phenylquinone (2-phenyl-1,4-benzoquinone) was suspended at the concentration of 0.08% (20 mg/25 ml) in maize oil according to the technique of Loux, Smith and Salem (Arzneim. Forsch. 28: 1644, 1978).

Experimental groups and phenylquinone administration experimental groups consisted of 8 animals (20-30 g), marked with picric acid (satured solution in alcohol). All animals of each group were treated i.p. with phenylquinone (10 ml/kg for animals of body weight over 25 g and 0.25 ml for animals of body weight under 25 g), placed in a transparent plastic cage (23.5×13.7×13.1 cm) and observed for a period of 20 min by experimenters unaware of the treatment.

Number and evaluation of writhings the observers recorded the number of writhings for each single animal by an automatic push-button counter.

Writhings were valued as follows:
complete=abdomen contraction, periodical trunk torsion and hind leg extension;

halves: abdomen contraction, sometimes with trunk torsion.

Every two half writhings the observer recorded one complete writhing.

Treatments compounds under evaluation were administered subcutaneously 20 min prior to phenylquinone. Every animal of each group received a different treatment.

The results obtained after s.c. administration of hydrochloride salts of dapiprazole and of morphine both alone and in association 20 minutes prior to phenylquinone (0.25 ml/mouse of a 0.08% suspension) injection are summarized in the table.

| Effects of dapiprazole and morphine, alone or in association, on phenylquinone writhing in the mouse. | | | |
|---|---|---|---|
| Treatment (s.c.) | Dose (mg/kg) | Writhing Mean & SD | % Inhibition versus control |
| saline | | 57.80 27.49 | |
| dapiprazole | 1 | 53.70 7.86 | −7 |
| morphine | 0.1 | 45.70 15.00 | −21 |
| | 0.3 | 28.30* 15.07 | −51 |
| | 0.9 | 2.10* 2.96 | −96 |
| morphine + dapiprazole | 0.1+1 | 40.60 15.50 | −30 |
| | 0.3+1 | 30.50* 17.77 | −47 |
| | 0.9+1 | 3.80* 5.27 | −93 |

* = significantly different from the control group (Anova): $P < 0.01$

At the dosage used (1 mg/kg) dapiprazole was completely devoid of analgesic activity. Morphine administered alone produced analgesic effects starting from 0.3 mg/kg (51% inhibition). The effect was more evident (96% inhibition) at the highest dose used (0.9 mg/kg).

No changes in the analgesic effects of morphine were observed when the two compounds were administered simultaneously.

EXPERIMENT B

Animals 300 female Swiss CD-1 mice (Charles River, Calco, Italy), weighing 28-33 g.

Housing the animals were housed twenty-five per cage in Makrolon cages measuring mm 590×385×h 200 and acclimatized to the animal housing for about 1 week before initiating the study. After treatment and during the observation period the mice were housed five per cage in Makrolon cages measuring mm 67×207×h 140. Animal room temperature was controlled at 21°±2° C., 12 air changes per hour. Natural daylight was supplemented with artificial illumination from 7.00 a.m. to 7.00 p.m.

Diet all mice had free access to tap water and standard laboratory rodent diet "4RF21", supplied by Italiana Mangimi, Settimo Milanese (Milan).

Treatment dapiprazole hydrochloride batch 5/A was dissolved in distilled water at five dosage levels (from 995 to 480 mg/kg) and administered subcutaneously in the right flank.

Morphine hydrochloride (ACRAF S.p.A., Rome) was dissolved in distilled water at six dosage levels (from 829 to 333 mg/kg) and administered subcutaneously in the left flank. For both compounds the ratio used between each dose level was 1.2. For each dose level, ten animals were used.

When combined, the doses were in proportion to their individual LD values as follows: 80%+20%; 60%+40%; 40%+60%; 20%+80% of dapiprazole hydrochloride and morphine hydrochloride, respectively. For each combination dapiprazole hydrochloride was given first, 5-10 seconds before morphine hydrochloride administration.

Observation

Toxyc symptomatology and mortality were registered during the first 4 hours following administration and then daily up to day 4. Complete autopsy was performed on all animals which died during the observation period and on the survivors sacrificed at term by CO asphyxiation.

$Ld_{50}$ calculations the LD50's and related values for the single agents were calculated according to Litchfield and Wilcoxon (1949).

EXPERIMENT C

A preliminary clinical trial was carried out on cancer patients suffering from pains calling for the administration of morphine.

A 1st group of patients received 10 mg of morphine hydrochloride alone by oral or parenteral route as many times a day as required by the respective pain syndrome.

A 2nd group of patients received a combination containing 10 mg of morphine hydrochloride associated with from 2.5 to 10 mg of dapiprazole hydrochloride by oral or parenteral route as many times a day as required by the respective pain syndrome.

The patients were asked about the effectiveness of the treatment and the daily administration was increased as the treatment lost its effectiveness.

After two months, the increase in daily administration required by patients treated with morphine hydrochloride plus dapiprazole hydrochloride was significantly lower than that required by patients treated with morphine hydrochloride alone.

What is claimed is:

1. A method for inhibiting the development of tolerance in the analgesic treatment with morphine of a subject in need of said treatment, comprising administering systemically and contemporarily an effective analgesic dose of morphine and an amount of dapiprazole of from ¼ to 1 part by weight to 1 part by weight of said analgesic dose of morphine.

2. A method as in claim 1, wherein the said analgesic dose of morphine is of from 8 to 20 mg.

3. A pharmaceutical composition comprising from 2 to 20 mg of dapiprazole or the equivalent amount of a pharmaceutically acceptable acid addition salt effective in inhibiting the development of tolerance, and an effective analgesic amount of morphine together with a pharmaceutically acceptable carrier.

4. A composition as in claim 3 wherein the amount of dapiprazole is of from ¼ to 1 part by weight to 1 part by weight of said analgesic amount of morphine.

* * * * *

UNITED STATES PATENT AND TRADEMARK OFFICE
CERTIFICATE OF CORRECTION

PATENT NO. : 5,041,446

DATED : August 20, 1991

INVENTOR(S) : Silvestrini, Bruno

It is certified that error appears in the above-identified patent and that said Letters Patent is hereby corrected as shown below:

On the title page,
[30] Foreign Application Priority Data, should be corrected to read:

--[30]    Foreign Application Priority Data

June 10, 1988 [IT]   Italy......................48071A/88--

Signed and Sealed this

Fifth Day of January, 1993

Attest:

DOUGLAS B. COMER

Attesting Officer      Acting Commissioner of Patents and Trademarks